United States Patent
Fougere

(10) Patent No.: US 9,410,910 B1
(45) Date of Patent: Aug. 9, 2016

(54) HYBRID CONDUCTIVITY SENSOR

(71) Applicant: Alan J Fougere, Falmouth, MA (US)

(72) Inventor: Alan J Fougere, Falmouth, MA (US)

(73) Assignee: D-2 INC., N. Falmouth, MA (US)

(*) Notice: Subject to any disclaimer, the term of this patent is extended or adjusted under 35 U.S.C. 154(b) by 106 days.

(21) Appl. No.: 14/286,557

(22) Filed: May 23, 2014

Related U.S. Application Data

(60) Provisional application No. 61/826,797, filed on May 23, 2013.

(51) Int. Cl.
*G01N 27/02* (2006.01)
*G01N 27/06* (2006.01)
*G01N 9/00* (2006.01)
*G01N 33/18* (2006.01)

(52) U.S. Cl.
CPC .............. *G01N 27/06* (2013.01); *G01N 9/00* (2013.01); *G01N 27/02* (2013.01); *G01N 33/18* (2013.01)

(58) Field of Classification Search
CPC ........ G01N 27/02; G01N 27/06; G01N 33/18
USPC ......................................................... 324/439
See application file for complete search history.

(56) References Cited

U.S. PATENT DOCUMENTS

| | | | | |
|---|---|---|---|---|
| 2,165,709 A | * | 7/1939 | Killian | H01J 61/28 313/231.01 |
| 3,701,006 A | * | 10/1972 | Volkel | E21B 21/08 324/436 |
| 3,926,056 A | | 12/1975 | Brown | 73/398 AR |
| 3,980,946 A | | 9/1976 | Fleury | 324/30 |
| 3,993,945 A | * | 11/1976 | Warmoth | G01R 27/22 324/434 |
| 4,019,134 A | | 4/1977 | Hogg | 324/71 |
| 4,220,920 A | | 9/1980 | Gross | 324/442 |
| 4,370,892 A | | 2/1983 | Schmoock | 73/861.12 |
| 4,740,755 A | | 4/1988 | Ogawa | 324/445 |
| 4,810,963 A | * | 3/1989 | Blake-Coleman | G01N 15/0266 324/204 |
| 5,157,332 A | | 10/1992 | Reese | 324/445 |
| 5,252,925 A | | 10/1993 | Matsumoto | 324/445 |
| 5,341,102 A | | 8/1994 | Akiyama | 324/445 |
| 5,455,513 A | | 10/1995 | Brown | 324/445 |
| 5,627,322 A | | 5/1997 | Osterloh | 73/861.22 |
| 5,959,455 A | | 9/1999 | Brown | 324/445 |

(Continued)

OTHER PUBLICATIONS

Fougere, Alan J, New Non-Ext. Field Inductive Conductivity (NXIC) Sensor . . . , [2000], IEEE Accession #6838823, pp. 1-10.

(Continued)

*Primary Examiner* — Jeff Natalini
(74) *Attorney, Agent, or Firm* — Milton Oliver

(57) ABSTRACT

A sensor for measuring conductivity of a fluid containing dissolved ions, particularly for measuring conductivity of salt water, features a cylindrical tube (57) of poorly conductive material such as glass, a first electrode (51A) and a second electrode (51B) inside the tube, connected together (56) to maintain a common electrical potential, a first transformer (52,53) concentrically arranged around the tube (57) to drive current through the fluid in the tube, and a second transformer (54, 55) arranged to sense a value of the current flowing in the fluid, and a digital processing circuit (62) coupled to receive an output signal of the second transformer, and to derive therefrom a value representing the conductivity of the fluid. The sensor is adapted to be towed behind a research ship, or to be deployed on an autonomous underwater vehicle (AUV) or the like. Current signals are preferably processed by digital switching measurement technology (dMST).

10 Claims, 12 Drawing Sheets

(56) References Cited

U.S. PATENT DOCUMENTS

| | | | |
|---|---|---|---|
| 6,369,579 B1 | 4/2002 | Riegel | 324/439 |
| 6,414,493 B1 | 7/2002 | Rezvani | 324/442 |
| 6,448,795 B1 | 9/2002 | Ermakov et al. | 324/724 |
| 6,603,320 B2 | 8/2003 | Higo | 324/702 |
| 6,720,773 B2 | 4/2004 | Brown | 324/449 |
| 7,275,420 B2 | 10/2007 | Discenzo | 73/54.28 |
| 7,541,004 B2 | 6/2009 | Niksa | 422/82.02 |
| 7,598,745 B2 * | 10/2009 | Hancock | G01R 27/22 324/439 |
| 7,965,167 B2 | 6/2011 | Volker | 336/229 |
| 8,420,363 B2 | 4/2013 | Wang | 435/173.1 |
| 8,440,093 B1 | 5/2013 | Nassef | 216/84 |
| 8,451,007 B2 | 5/2013 | Wang | 324/445 |
| 8,456,178 B2 | 6/2013 | Wang | 324/654 |
| 8,508,234 B2 | 8/2013 | Wang | 324/537 |
| 8,521,442 B2 | 8/2013 | Wang | 702/30 |
| 8,547,110 B2 | 10/2013 | Kesil | 324/633 |
| 8,552,750 B2 | 10/2013 | Fougere | 324/691 |
| 8,558,557 B2 | 10/2013 | Eberheim et al. | 324/654 |
| 8,581,575 B2 * | 11/2013 | Eberheim | G01N 27/023 324/204 |
| 8,594,781 B2 | 11/2013 | Chetham | 600/547 |

OTHER PUBLICATIONS

Sea-Bird Electronics, Appn-Note-93, "CTD Basics," Dec. 2013, retrieved May 13, 2014 from www.SeaBird.com, pp. 1-6.

MultiDimension Technology Co Ltd. datasheet, MMLH45F TMR Linear Sensor, retrieved Aug. 11, 2014 from www.dowaytech.com, pp. 1-3.

* cited by examiner

Electrical Equivalent Brown MKIIIB
Conductivity Sensor

HYBRID CONDUCTIVITY SENSOR

CROSS-REFERENCE

This application claims priority from my U.S. provisional patent application Ser. No. 61/826,797 filed 23 May 2013.

FIELD OF THE INVENTION

The present invention relates to the development of an improved conductivity sensor for the measurement of salinity and density, particularly in the ocean. More specifically, the present invention is a new hybrid conductivity sensor (fluid electrical conductivity sensor) that meets the general industry needs for rugged, accurate, small, physical oceanographic sensors for use on the widening set of AUV (Autonomous Underwater Vehicle), and UUV (Unmanned Underwater Vehicle) oceanographic research tools, particularly those used at high latitudes.

BACKGROUND

Electrical conductivity of a fluid is measured by applying a known voltage across defined volume of the fluid and measuring the subsequent electrical current that flows. There have been a number of different of sensors and methods used, to make this basic physical property measurement of a fluid. Each prior art device has been developed to overcome various physical limitations in making an accurate fluid conductivity measurement. The invention herein relates to an improved geometry and to an electrically-implemented sensor for measuring the electrical conductivity of seawater, as it relates to the field of physical oceanography. A primary tool for a physical oceanographer is an electrical Conductivity, Temperature, and Depth, (CTD) instrument, whose output signals can be used to compute the salinity and density of seawater through an accepted "equation of state" based on these three physical property measurements.

In 1961, the now-deceased Neil L. Brown, the "father" of the modern CTD instrument developed a Salinity, Temperature, and Depth, (STD) instrument. The "STD" was developed prior to low-cost modern computers, so the ability to compute salinity and density in real-time at the ocean surface was limited. Brown, in a novel electronic circuit, implemented in his instrument, allowed the value of scientific interest, namely salinity, to be derived from the three primary measurements of electrical conductivity, temperature, and, depth (pressure) measured from seawater. This instrument measured CTD, but, since the instrument implemented the "salinity equation" in internal analog electronics, and those Salinity, Temperature, and Depth values were transmitted to the surface, the instrument became known as an "STD."

According to generally-accepted industry terminology, a "contacting-type sensor" is one which uses electrodes in order to make the connection to the volume of fluid being measured, while a "non-contacting-type sensor" is one which uses inductive coupling, or similar non-electrode means, to measure the fluid whose properties are being evaluated.

The STD used an inductive non-contacting conductivity sensor; this sensor is depicted in FIG. 1. FIG. 1A depicts the equivalent electrical circuit. It can be seen, in FIG. 1, that the measured volume of seawater is a combination of the enclosed volume in the tube 12 between the two magnetic cores 11 and 15, with windings 13 and 17 and of a volume of water forming the return path around the outside of the cores 18.

Two aspects of this sensor limited its commercial application to the measurement of the oceanographic salinity and density. First, the large thermal mass of the sensor in relation to the volume of water which passed through the inside, which resulted in thermal error in the conductivity measured. Electrical conductivity of a fluid is highly dependent upon the temperature at which the conductivity is measured. If, due to the presence of the thermal mass of the sensor, a conductivity sensor heats or cools the volume of water which it is trying to measure, an inaccuracy of the computed salinity/density will result. Because oceanographic sensors are often used at substantial depths, where ambient water pressure can be as high as 700 Bar, the sensor magnetic cores were mounted in a pressure protecting metal housing. The pressure protecting housing 19 then needed to be coated with a dielectric material, in order to prevent the metal housing from forming a shorted turn around the sensor.

Secondly, the large non-contacting external field 18 can be affected by other structures associated with the CTD instrument, such as auxiliary sensors, protection frames, etc. These external structures alter the free current flow through the seawater. Hence, their influence cannot be distinguished from changes in the seawater conductivity, and introduces a confounding variable.

In 1970, Brown again developed an improved instrument which used a 4-electrode conductivity sensor, the MK IIIB CTD, disclosed in U.S. Pat. No. 3,939,408, the conductivity sensor for this instrument illustrated schematically in FIG. 2. The MK IIIB CTD utilized a 4-electrode conductivity cell where the electrodes E1 and E2 were deployed inside and two electrodes E3 and E4 were deployed outside a small (4 mm square alumina tube×3 cm long) head piece 21. In this "contacting-type" conductivity cell, the electrodes and tube are configured in a traditional "four-terminal resistance measurement" manner. "Four-terminal resistance measurement" is an industry term. It refers to the measurement of resistance, where a known current is passed through one set of leads connected to the resistance in question. A second set of leads, connected at the same point to the resistance, is used to measure the voltage across the unknown resistance. The resistance is then computed using Ohm's Law V=I*R.

A four-terminal resistance measure is advantageous, in that the resistance of the measuring lead wires does not affect the measured result. Hence, connectivity sensors based on four terminals of measure can eliminate, from the calculation of the fluid conductivity, confounding variables arising from both lead wire, and from the more-difficult-to-stabilize impedances of the electrodes.

It can be seen in FIG. 2 that electrodes E3 and E4 are mounted outside the fixed volume of the square sensor head tube 21. As such, a portion of the measurement volume is "outside" the head piece. A significant portion (~80%) of the measured resistance of seawater is from the restricted volume of seawater located inside the head piece tube 21. The MK IIIB CTD and sensor had significant commercial success and was the instrument that established CTD's as the primary tool in gathering high resolution oceanographic density/salinity data. Since the original design goal of the MK IIIB was to provide very high vertical resolution salinity/density profiles, the small size of the MK IIIB conductivity sensor, combined with its partial external field, were acceptable technical tradeoffs vis-a-vis the desire to attain absolute measurement stability. It became an accepted common scientific practice to "correct" or "compensate" CTD data, based upon measurements made on discrete water samples that were collected at the same time. The small length of the MK IIIB sensor provided a sensor with a short flushing interval, such that it had a rapid response to changes in conductivity. It was known as a "micro-structure" sensor. The high speed response was problematic for users, since it required complex time/data matching to slower-responding temperature probes. This conductivity-temperature time constant mismatch led to computed salinity/density "spikes" or "anomalies" in the resultant oceanographic profiles.

In 1968, Art Pederson introduced a conductivity sensor, shown in FIGS. 3A, 3B, 3C, based on an 18-cm-long by 4 mm diameter PYREX glass tube 31, into which 3-electrodes are mounted axially. The resultant configuration of the sensor and the connection of its electrodes was to form two resistive cells in parallel. This is depicted in FIG. 3C, the electrical equivalent model. In the Pederson cell, the two outer electrodes E2 and E3 are tied together; as such, it is essentially a two-electrode sensor, i.e., V1 and C1 is one electrode, and V2 and C2 is the electrically tied E2 and E3 electrode. The parallel nature of the configured tube and electrodes results in a very low impedance cell, since the two resistive paths Rw1 and Rw2 are electronically tied in parallel, therefore reducing the effective resistance of the sensor by (½) one half.

In order for Pederson to overcome the low impedance, a glass tube 31 was chosen, with a small inner diameter and a longer length. These design choices resulted in a "soda straw" sensor which had the disadvantage that generally a sample pump was needed to get the seawater sample to move through the sensor. From FIG. 3C, it can be seen that the contact impedance of the three electrodes is also included in the measured resistance path. Therefore, electrodes E1, E2, and E3 must have very low impedance, in comparison to the impedance Rw1 and Rw2 of the seawater to be measured.

Also, the contact impedance of all three electrodes must be stable, since changes in the contact resistance cannot be differentiated from changes in the measured conductivity of seawater. To address the contact impedance issue, Pederson increased the size and surface area of the electrodes, and fabricated them from a precious metal, namely platinum. To further reduce the contact impedance, Pederson applied a platinum-black coating which serves to increase the effective surface area. In a later novel development by Pederson, an associated temperature sensor was included in the flow path of the pumped sensor, to help reduce the time-constant mismatch between the conductivity sensor and the temperature sensor; this resulted in improved computations of salinity and density, using the "equation of state" for seawater.

Despite difficulties in obtaining sufficient flow through the Pederson sensor, the feature of a fully enclosed volume combined with the feature of reducing the time-constant mismatch, has resulted in instruments based on the Pederson conductivity sensor becoming the physical oceanographer's instrument of choice. This sensor has had long-term commercial success and dominates the current commercial market for CTD instrumentation.

The Pederson sensor has demonstrated that electrodes can be built with sufficiently low impedance, which are also suitably stable, such that they can be included in the electrical measurement path without interfering with the desired measured result. However, in low-power, slower-moving deployment platforms, such as the aforementioned AUVs and UUVs, the requirement, that a pump be used, with its attendant power demands, has limited the adoption of the Pederson technology on these newer research deployment platforms.

In 1999 Brown obtained U.S. Pat. No. 5,959,455, assigned to Falmouth Scientific, Inc., for a novel Non-External Field Inductive Conductivity (NXIC) sensor, shown in FIGS. 4 and 4A. The concept of this oceanographic conductivity sensor was to eliminate a negative aspect of the traditional non-contacting inductive sensor, by fully containing the measurement current field within the defined volume of the sensor.

FIG. 4 shows the Brown sensor, which relied on two tubular fluid paths 41 and 42, each path with a traditional dual-core, T1 & T3 and T2 & T4 respectively, inductive conductivity sensor. The drive cores T1 and T2, located on each tubular path, are matched and driven in opposition, such that the current which flows in each tube 41 and 42 is equal. The ends of the tubes are connected by structures (shrouds 43 and 44) that further assist in containing the measured current field within the prescribed volume of the sensor. The resistance of seawater contained in the first tube 42 is represented electrically by R1; similarly, the resistance of seawater in tube 41 is represented by R2. The resistance of the seawater around the outside of the sensor is represented by R3. Hence the current flowing in tube 42 due to the drive core induced voltage T1 is I1, and respectively the current flowing in the opposite direction as created by T2 in tube 41 is I2. The current that wants to flow through the seawater on around the outside of the sensor is depicted as I3. The electrical equivalent of the sensor is shown in FIG. 4A, where it can be shown that the potential at each end of the sensor must be equal (Point A & Point B), (in a manner similar to the Pederson sensor where the ends are connected electrically, to retain the same potential). This is the result that drive transformer T1 and T2 are driven in parallel as such generate equal "drive" voltage in their respective tubes 42 and 41. In addition, tubes 41 and 42 have identical diameter and length and thus have equivalent volume, holding equal volume of the same seawater, hence the current I1 is then equal and opposite to I2. As such, the tendency, for the measurement current I3 to return via the outside of the sensor through R3, is significantly reduced. The NXIC sensor has had moderate commercial success. Its limitations are its complex construction and its cost, due to the large number of elements. Another limitation is that the bulk mass of the sensor results in a significant thermal contamination of the seawater measured within its volume.

There have been a number of other electrode-based oceanographic conductivity sensors. Some of these other sensors are based on as many as 7 electrodes, all aimed at overcoming issues having to do with polarization, reduction of electrical interference of the electrodes on the measurement, and, of course inventive designs to try and minimize internal versus external fields, etc. A variety of 2-electrode to 4-electrode sensors, deployed in various geometries, have also been disclosed.

Another significant problem with oceanographic sensors is the potential for biological fouling, such as marine organisms which adhere to the sensor, and distort or obstruct its normal operation. Various measures have been used, with differing levels of success, to try to deal with this problem. Biological protection is required in a conductivity sensor due to the fundamental requirement of conductivity measurement, that it is the measurement of conductance through a 'known' well-defined volume. Biological contamination can degrade the measurement volume, leading to measurement errors. Additionally, biological fouling on the electrical current-collection electrodes can alter the near-field electrical current flow in a way which cannot be distinguished from changes in the electrical conduction due to the fluid in the sensor. The same is true for the voltage electrodes, biological fouling can alter the shape of field lines again resulting in measurement errors.

It is the author's opinion that internal-field sensors which are commercially available have demonstrated better commercial acceptance, due the combined aspects of a well defined measurement volume and their ability to be protected from biological fouling. The well-known and commercially successful sensors are then the well-known model from Seabird Electronics Company, Seattle Wash., which uses a 3-terminal-electrode-type contact sensor, and the lesser-known FSI (Falmouth Scientific Inc.) NXIC non-contacting sensor. As described, the latter sensor uses two inductively coupled type cores, positioned in opposition to each other, in order to eliminate (reduce) any external field.

SUMMARY OF THE INVENTION

In order to overcome, or at least minimize, the aforementioned problems, a new conductivity sensor has been developed, which combines some features of prior art contacting-type sensors with some features of non-contacting-type sensors. This "hybrid" conductivity sensor delivers measurement accuracy which is competitive with current commercially available conductivity sensors, at a fraction of the size, weight, and power requirements of those prior art sensors. Due to the structure of the new sensor, in most instances no supplemental pump will be needed to assure adequate through-flow. The sensor can be deployed in a traditional lowered or towed-by-cable manner and/or moored, as are other commercially available sensors.

DETAILED DESCRIPTION OF THE PREFERRED EMBODIMENTS

Figure 1:
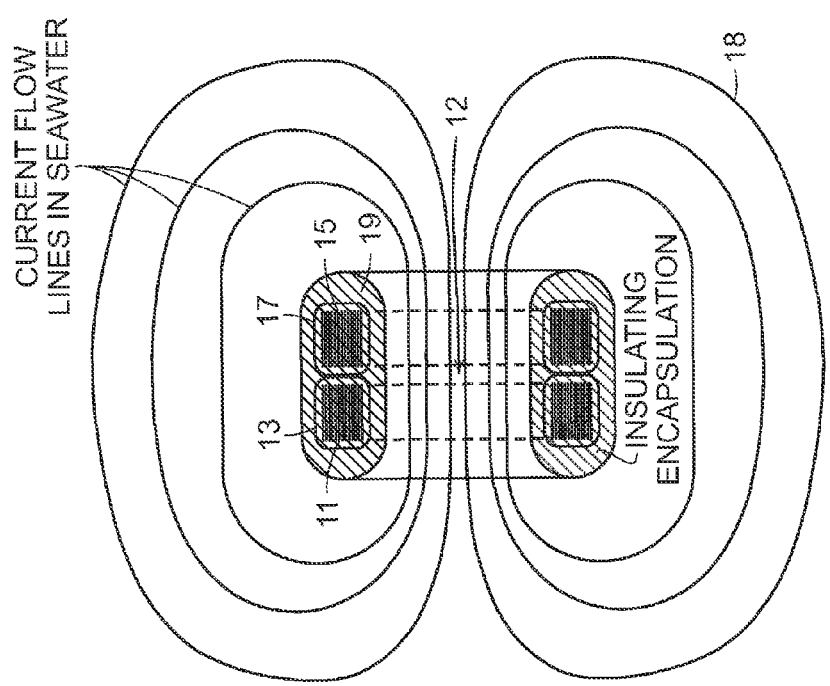
FIG. 1 is a view, partially in section, along with an electrical model of a prior art non-contacting-type (inductive) internal/external field conductivity sensor.
Figure 1A:
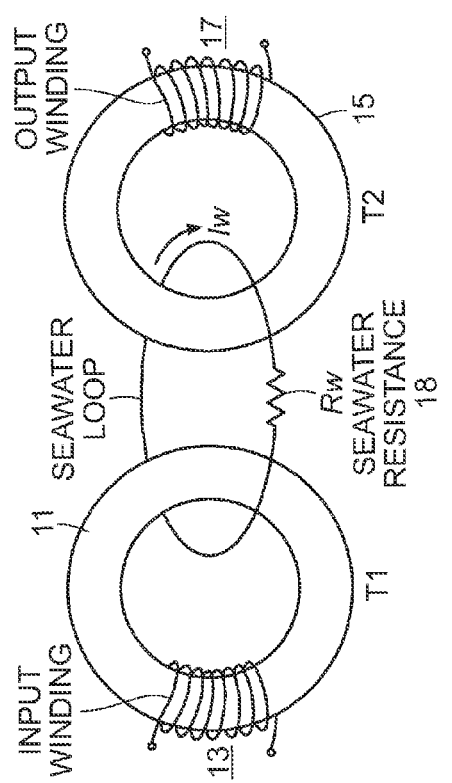
FIG. 1A depicts the equivalent electrical circuit.
Figure 2:
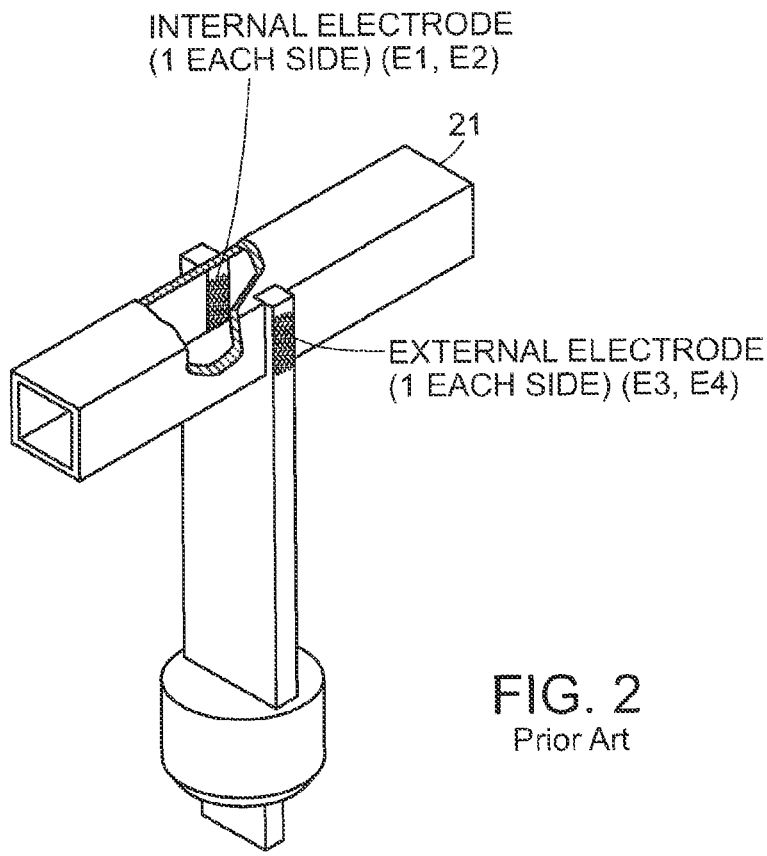
FIG. 2 is a schematic diagram of a prior art contacting-type 4-electrode internal/external field conductivity sensor and FIG. 2A is an electrical schematic diagram thereof.
Figure 2A:
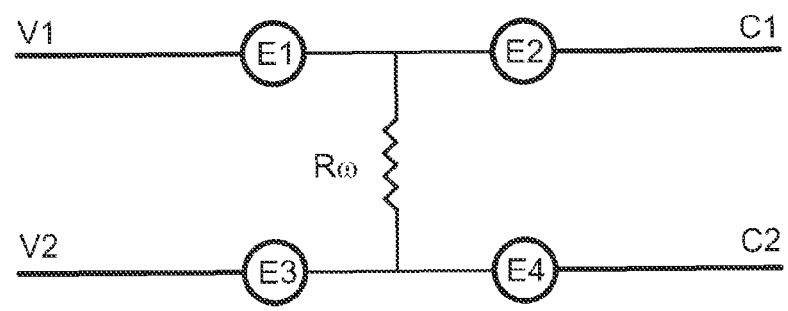
Figure 3C:
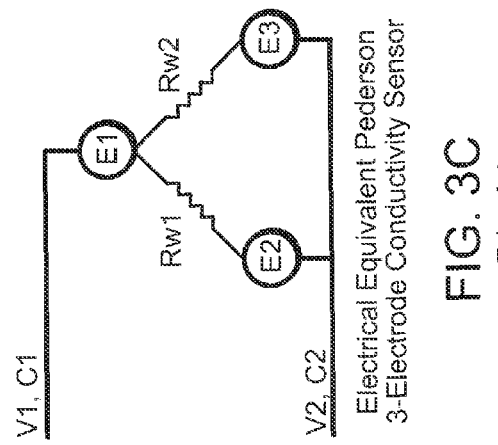
FIG. 3C is an electrical schematic diagram thereof.
Figure 3A:
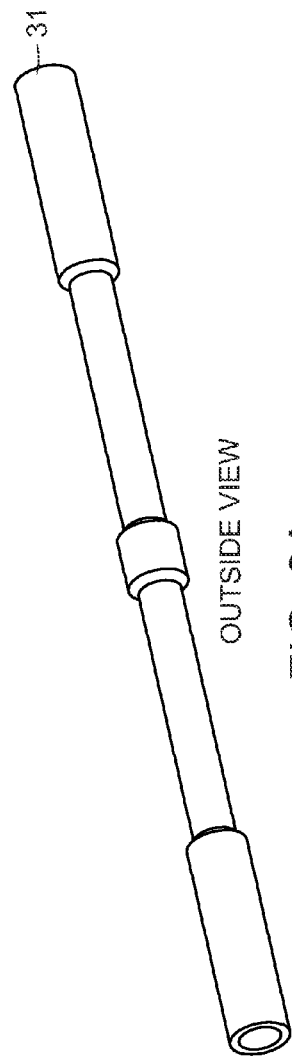
FIGS. 3A and 3B are diagrams, partially in section of a prior art contacting-type 3-electrode internal field conductivity sensor.
Figure 3B:
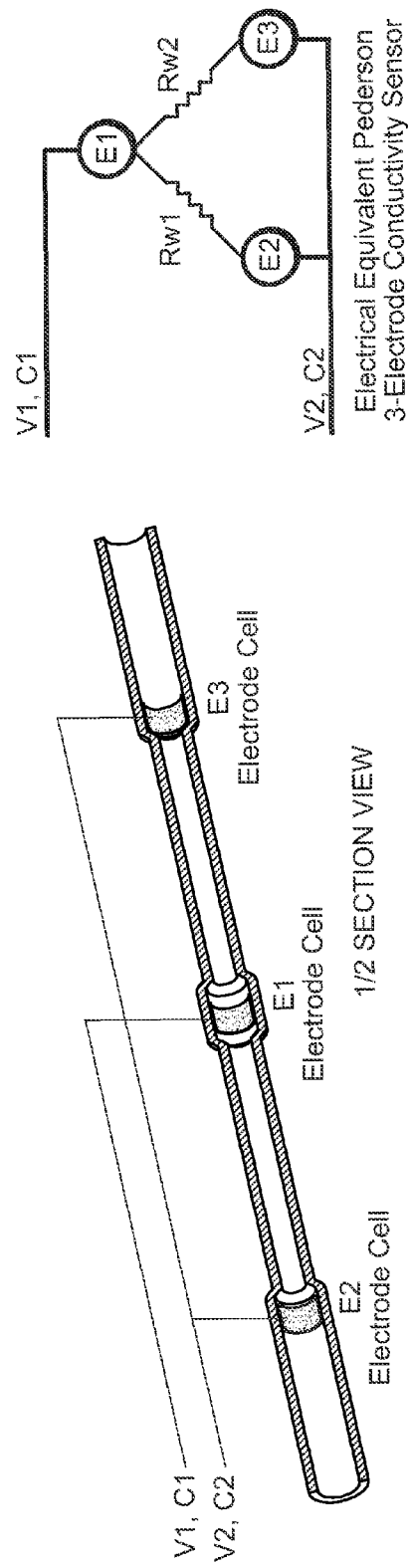
Figure 4:
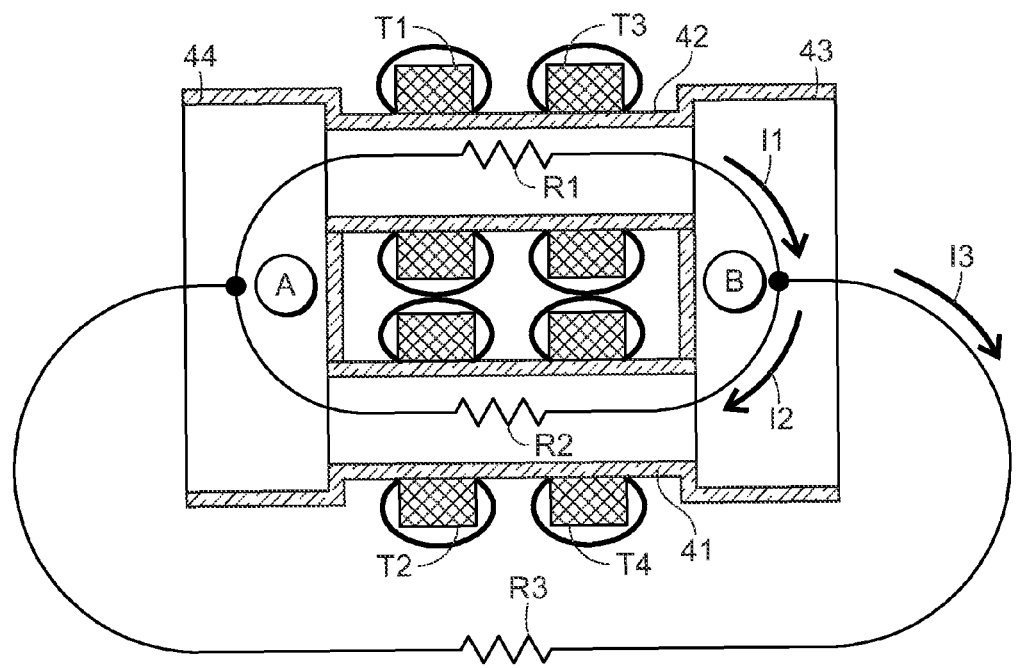
FIG. 4 is a view, partially in section, of a prior art non-contacting-type (inductive) internal-field conductivity sensor.
Figure 4A:
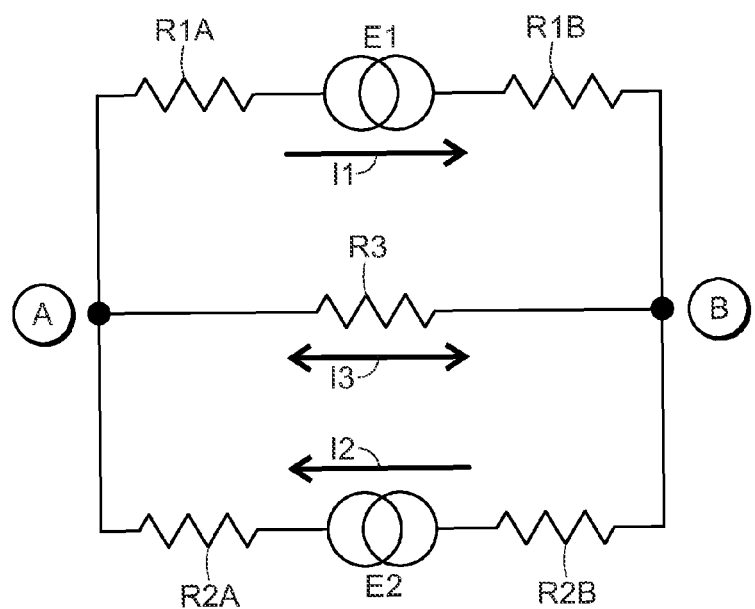
FIG. 4A is an electrical schematic diagram thereof.
Figure 5:
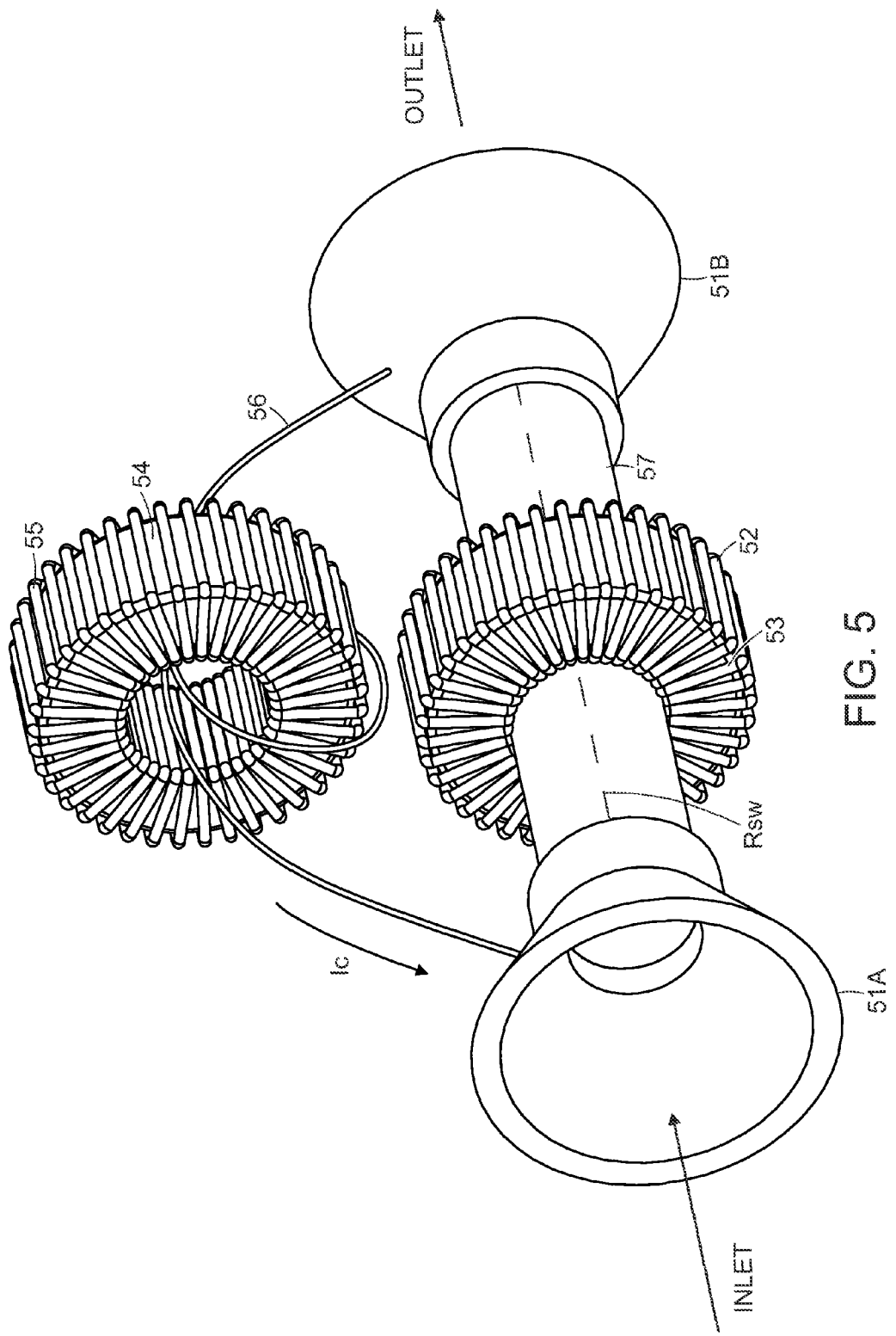
FIG. 5 is an outside view of the hybrid electrode and inductive conductivity sensor, in accordance with the present invention.

FIG. 5 is a perspective view of a preferred embodiment of the hybrid conductivity sensor of the present invention. The structure of the sensor is based on two design requirements: 1) the volume must be carefully controlled, i.e. be fully enclosed, be stable in spite of changes in pressure and temperature, and 2) electrodes designed to be used in the measurement volume must be physically and electrically stable, so that changes in the properties of the electrodes themselves do not affect the measurement in a difficult-to-predict manner.

The United Nations Educational, Scientific & Cultural Organization (UNESCO) has a Scientific Committee on Oceanographic Research (SCOR). In 1988, UNESCO published a document from its SCOR Working Group 51 which specified minimum requirements for the acquisition, calibration and analysis of Conductivity, Temperature and Depth (CTD) data. The sensor of the present invention satisfies the UNESCO requirements for both dynamic and static precision.

The hybrid cell relies on a precision-bore glass tube 57 as the fundamental volume control element. Unlike other tubular cells, the sensor has a reasonable diameter-to-length ratio, to allow it to naturally aspirate; sensitivity is gained in the electronic analysis circuits discussed below. The measured-volume-defining tube is placed through a toroid drive transformer 52, with drive winding 53. This transformer 52 & 53 is used to generate a voltage in the fluid contained in tube 57. The voltage results in a current flow Ic in the fluid; this is the same effect as the well-known contactless conductivity sensor more commonly referred to as an "inductive" conductivity sensor. The ends of the glass tubes are mounted and sealed into electrodes 51A & 51B composed of a suitable metal (e.g. titanium), or a set of annular electrodes are mounted around the inner circumferences of the glass tube 57.

Suitable metals are ones where the surface impedance, in relation to its contact with seawater, remains stable; materials that oxidize or form non-conductive layers would not be suitable for the purposes of forming an electrode connection to the seawater measured. These suitable materials are noble metals, such as platinum, gold, silver, and other precious metals.

The two end electrodes 51A & 51B are tied together by a low-impedance conductor 56, that is, an electrical conduction path which is low in its impedance as compared to the external path around the outside of the sensor via the seawater which does not pass through the sensor. The pair of electrodes 51A & 51B must remain at the same electrical potential since they are electrically tied together by the conductor 56. In this manner, the electrodes 51A & 51B and electrical connection 56 provide two essential sensor functions, 1) they form a current return path for current induced in the sensor by the induced voltage that flows in proportion to resistance Rw formed by seawater contained within tube 57, and 2) they effectively short out any external (outside the sensor) current return path which would alter the current measured in the sensor. The current that flows in the cell is therefore dependent only on the resistance of sea water Rw that is inside the glass tube between the end "electrodes" 51A & 51B.

The return path wire 56 is subsequently wound around a current measurement core 54 with winding 55, to enable measurement of the electrical current flowing in the shorting wire 56 which has been shown to be identical to the current Ic flowing in the measured seawater. This type of current measurement is well demonstrated and reduced to art as exemplified by prior U.S. Pat. No. 5,455,513 (Brown & Fougere).

Figure 6:
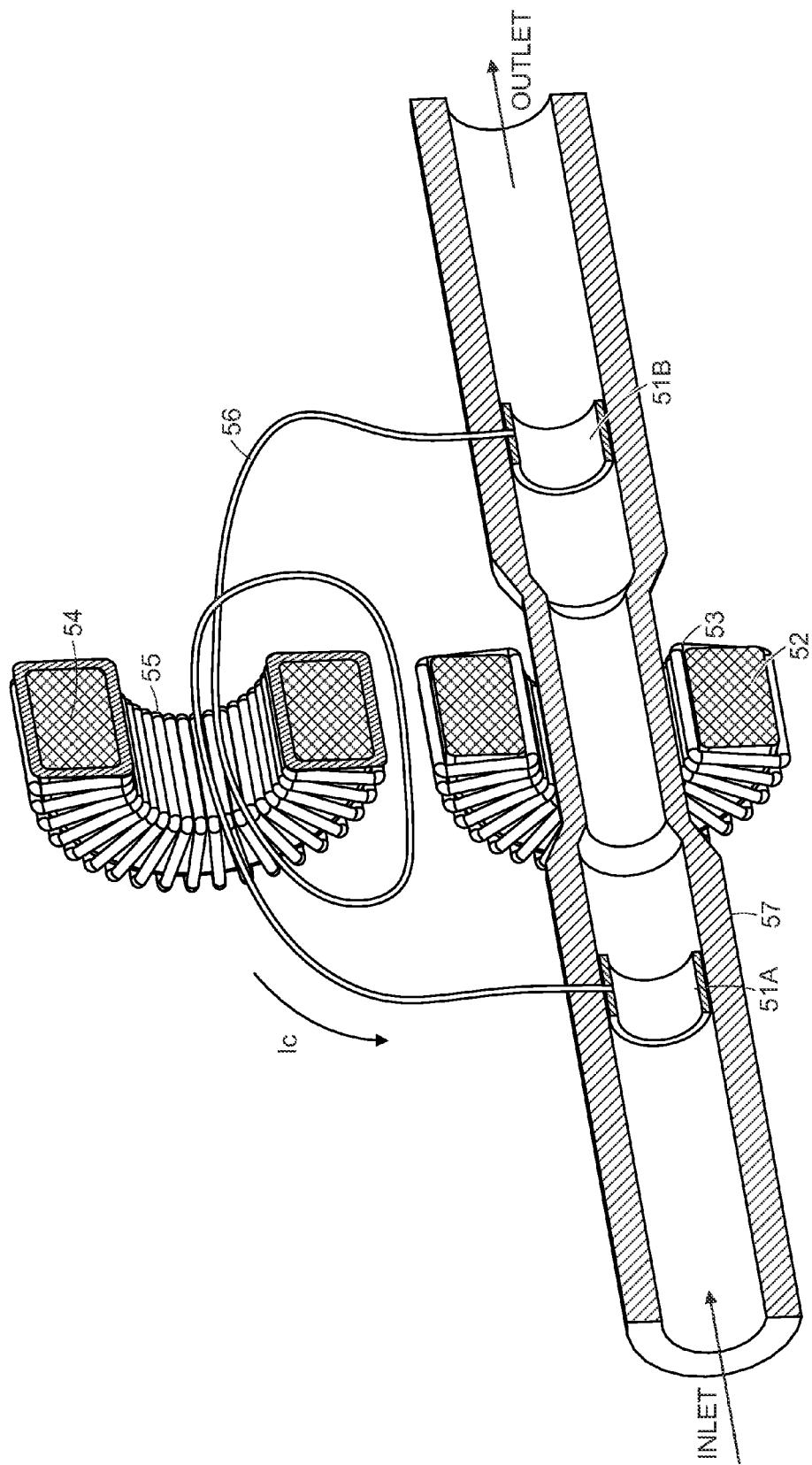
FIG. 6 is a view, partially in section, of the hybrid electrode and inductive conductivity sensor, in accordance with the present invention.

FIG. 6 illustrates an alternative embodiment of the hybrid sensor, according to which smaller less-thermally-intrusive end electrodes 51A & 51B can be provided. By incorporation of the electrodes 51A & 51B located inside the diameter of volume-controlling tube 57, which is also extended past the electrodes, such extension adding additional resistance to the external resistive path, a similar result can be expected. The smaller, less thermally intrusive version of electrodes 51A & 51B reduces the impact of the thermal mass of the sensor on the measurement since the electrical conductivity of fluids is highly temperature dependent, the optimum conductivity sensor then measures the conductivity of the fluid, without altering the temperature that the fluid is at. In the present implementation, the glass tube 57 is 4" long (100 mm), extended ends 0.31" dia (8 mm)×1.5" (37 mm) long, with center measurement section of 0.20" dia (5 mm)×0.75" long.

Figure 7:
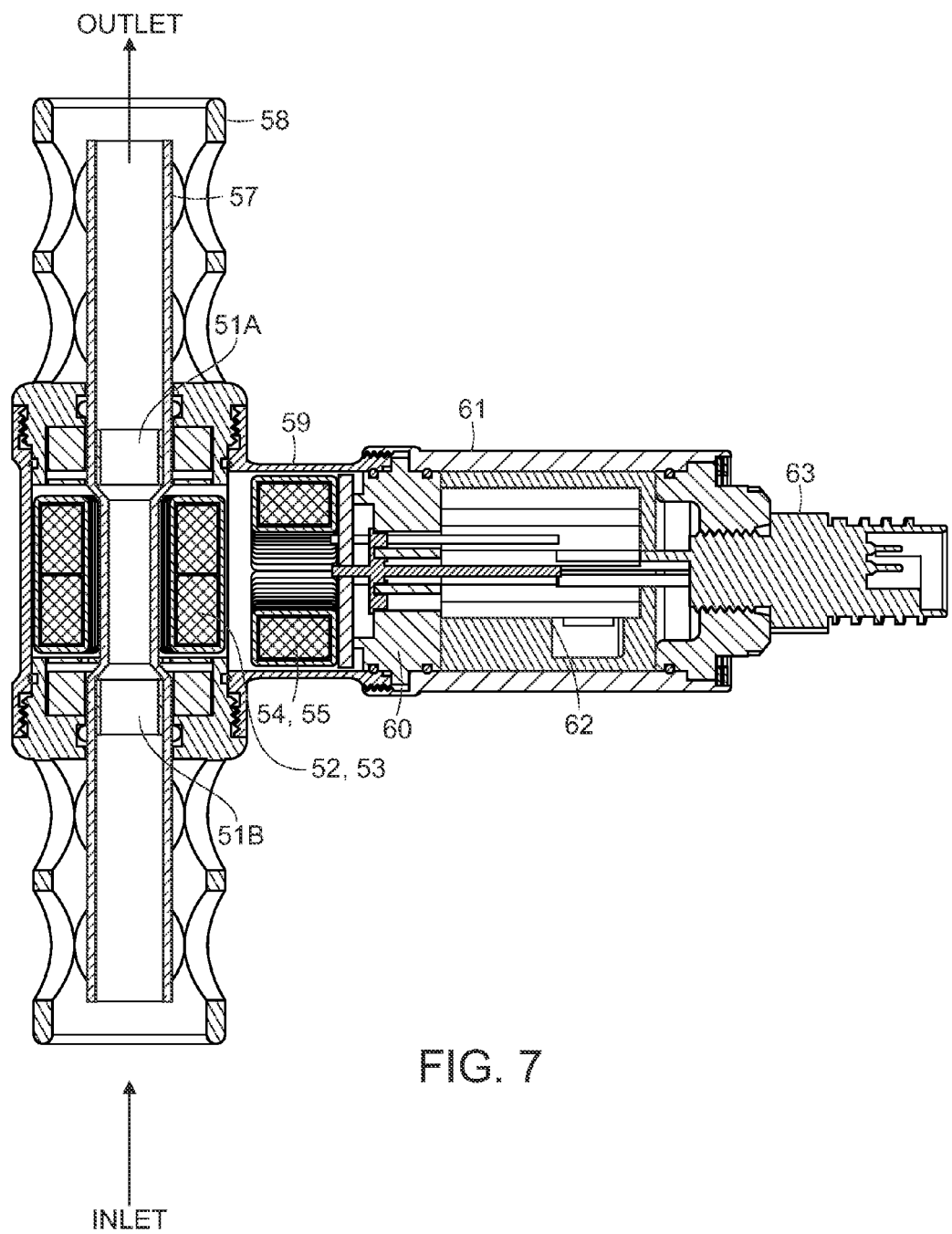
FIG. 7 is a view, partially in section, of one embodiment of the hybrid electrode and inductive conductivity sensor, in accordance with the present invention.

Clearly, in a uniform thermal bath where the sensor and the fluid have been allowed to thermally equilibrate, there is no effect of the thermal mass of the conductivity sensor on the temperature of the fluid. However, in practice, the temperature of the ocean typically declines as one profiles from the surface to the bottom; hence the conductivity sensor is always warmer than the water which is passing through it during the lower, and it is typically colder than the water as the sensor is returned to the surface. The conductivity sensor cools by the transfer of its stored internal heat to the water that is passing through the sensor. The rate of the heat passing into the fluid is dependent upon the thermal mass of the cell, upon the ratio of the wetted area of that thermal mass to the water volume passing through it, and upon the temperature difference. In the Pederson cell (as described in the article "Thermal Inertia of Conductivity Cells" by Rolf. G. Lueck and James J. Picklo, Journal of Atmospheric and Oceanic Technology, Volume 7, pp. 756-768, Amer. Meteorological Society, October 1990) there is a large wetted-area-to-volume ratio; hence, the effects of the thermal mass of the sensor are enhanced. A fundamental feature of the hybrid conductivity sensor of the present invention is that it has a low thermal mass, with an improved wetted-surface-area to volume, as compared with traditional 3-electrode internal field sensor implementations. In the Hybrid Conductivity Sensor (HCS) disclosed herein, the physical implementation reduces the thermal contamination of the sample measured, and hence improves the dynamic accuracy of the sensor in determining oceanographic salinity/density. This can be seen in the sensor depiction which is shown in FIG. 7. In this version of the sensor, smaller electrodes 51A & 51B are incorporated inside the same glass tube 57 that defines the "measurement" volume. The external impedance path is increased in value, by extending the glass tube past the smaller electrodes, preferably for a distance of equal or greater than 4 times the inner diameter of the tube 57. The combination of smaller electrodes and extension of the external impedance path results in ideal performance, with 100% of the current, induced by the drive core 52 with winding 53, being collected by the smaller electrodes. Again, the external path is eliminated, since the two end electrodes are held at a common electrical potential by the wire 56 which connects them.

In practice, FIG. 7 provides a more economical embodiment, since the physical size of electrodes 51A & 51B that must be fabricated from precious metals is significantly reduced. This configuration does result in a longer fluid-flushing time period; however, the adjustment of the internal-diameters-to-length ratio can be optimized, to attain both adequate current collection and reduction of the external field and reasonable fluid-flushing time periods. In the present implementation, the dimensions of central glass tube 57 are detailed above; all elements are in proportion to tube 57, as is shown in FIG. 7.

In FIG. 7, the present implementation of the HCS technology, the glass measurement tube 57 is shown mounted in a protective housing 58. The tube has annular electrodes 51A & 51B which are recessed in from the ends of tube 57. The current-drive core 52 with winding 53 is mounted concentrically around glass tube 57 and is protected by housing 59. Current measurement core 54 with winding 55 is mounted onto a connecting end cap 60 and connected to an input of an electronic circuit 62 which is mounted in a surrounding pressure-protecting housing 61. An electrical connector 63 connects from an output of circuit 62 to transmit sensor data to the sensor user, for example a researcher on the ocean surface.

HCS Conductivity Sensor Electrical Model

Figure 8:
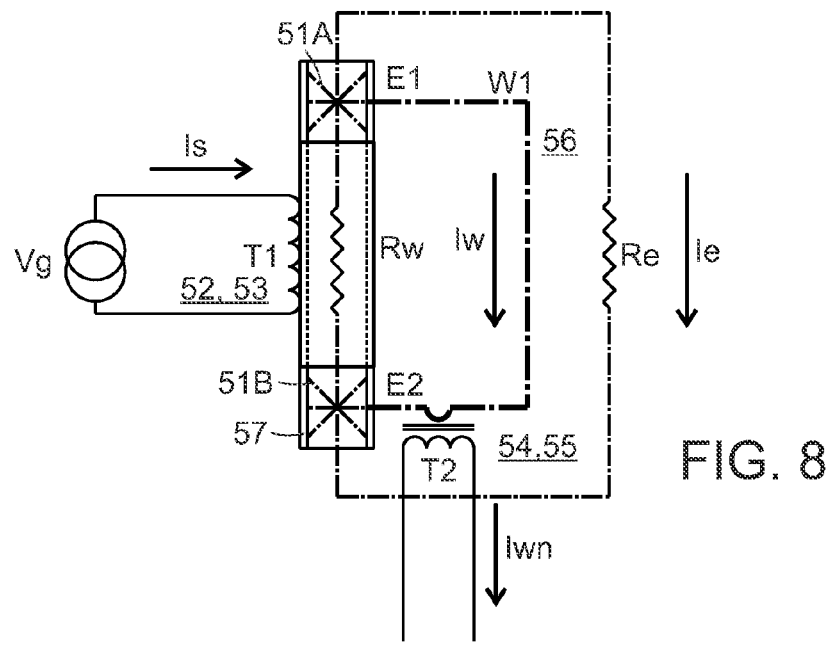
FIG. 8 is an electrical schematic diagram thereof.

FIG. 8 schematically illustrates an electrical equivalent model of the sensor. In FIG. 8, the sensor is driven by an AC generator represented by Vg and the core 52 (with winding 53) is placed concentrically around the main sensor tube 57. The tube 57 forms the enclosed well-defined measurement volume. A current Iw flows through the sensor, in inverse proportion to the resistance of the sea water represented by Rw. This current is collected by the sensor tube end electrodes 51A & 51B (E1 & E2 respectively) which are connected together by a very low impedance wire 56 (W1). W1 is passed around (either one or more turns) current sensing transformer T2 with magnetic core 54 and winding 55. The current flowing through this winding in current sensing transformer results in current Iwn in the secondary winding of the transformer. Current Iwn is proportional to the sea water current, by a factor corresponding to the number of turns in the transformer. The external path around the outside of the sensor is represented by resistance Re. Since electrodes 51A & 51B (E1 and E2) are connected by a very low-impedance wire 56 (W1), the electrical potential at E1=E2; hence, the external current driving voltage is equal to zero (0). Since the driving voltage across the external resistance Re is zero, the current Ie in the external path can be found by Ohm's law, Ie=E1−E2/Rw=0.

Hence the effective circuit-presented impedance of Rw is infinite and no current flows in the external path Re. The electrical connection of E1 to E2 effectively shorts out the external current path. In practice, the external current flow is proportional to the ratio of the external sea water resistance path to the direct current path represented by the resistance of wire W1, which includes any polarization impedance of electrodes 51A & 51B; by design, this can be made to be very low. For example, in the present implementation, the resistance of path 56 (W1) can be made very small, for example <0.1 ohms. The ability of electrodes 51A & 51B (E1 and E2) to collect all current Iw flowing in the sensor resistance Rw can be enhanced by increasing the surface area of the electrodes 51A & 51B, by increasing the effective surface area, by process treating them with a gold- or platinum-black or by another established conductive-surface treatment. Additional impedance ratio improvements can be made as diagramed in FIG. 9; here, the external sea water resistive path resistance can be increased by adding insulating structures 64 axially beyond the electrodes 51A & 51B, at the tube ends; the effect of the extension is added to the equivalent circuit (FIG. 8) and is shown in FIG. 9.

Figure 9:
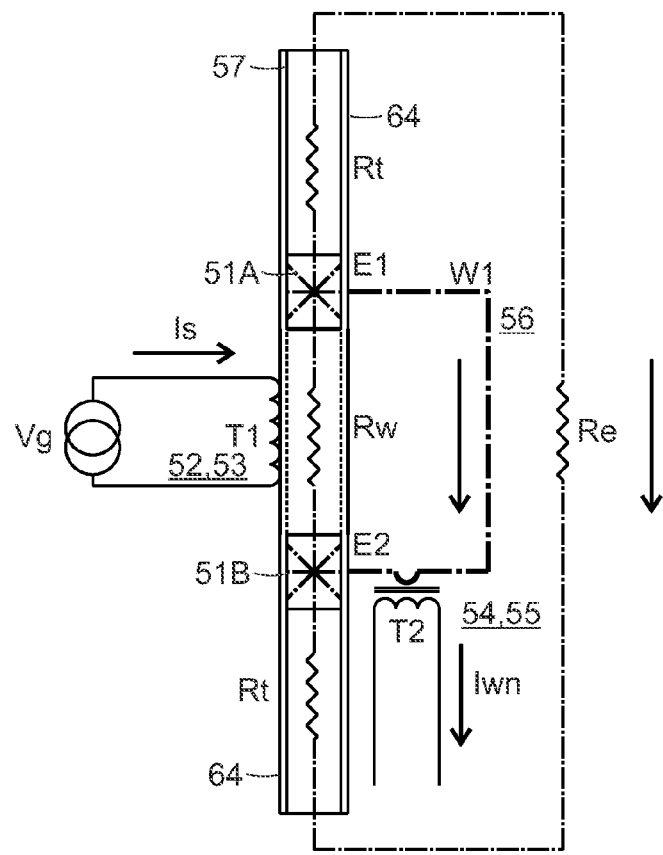
FIG. 9 is a diagram illustrating the benefits of an extended-tube embodiment of the hybrid electrode and inductive conductivity sensor, in accordance with the present invention.

In FIG. 9, the effect on the electrical model of extending the glass tube 57 beyond the electrodes 51A & 51B (E1 and E2) is detailed. In this embodiment, an additional impedance Rt at both ends of the sensor is the result of an extended glass tube 64 added axially to the base glass tube 57. The total external path resistance is increased compared to the prior embodiment, and is now the sum Re=Re+2*Rt. The increased impedance allows the physical size of the electrodes 51A & 51B (hence the current collection impedance represented by E1 connected to E2) to be reduced. In turn, this decreases the physical amount of material used to form the electrodes 51A & 51B. The sensor as detailed in FIG. 9 is the preferred embodiment, since it reduces the size of, and the amount of precious metal needed to construct, the critical current-collection electrodes 51A & 51B.

Figure 10:
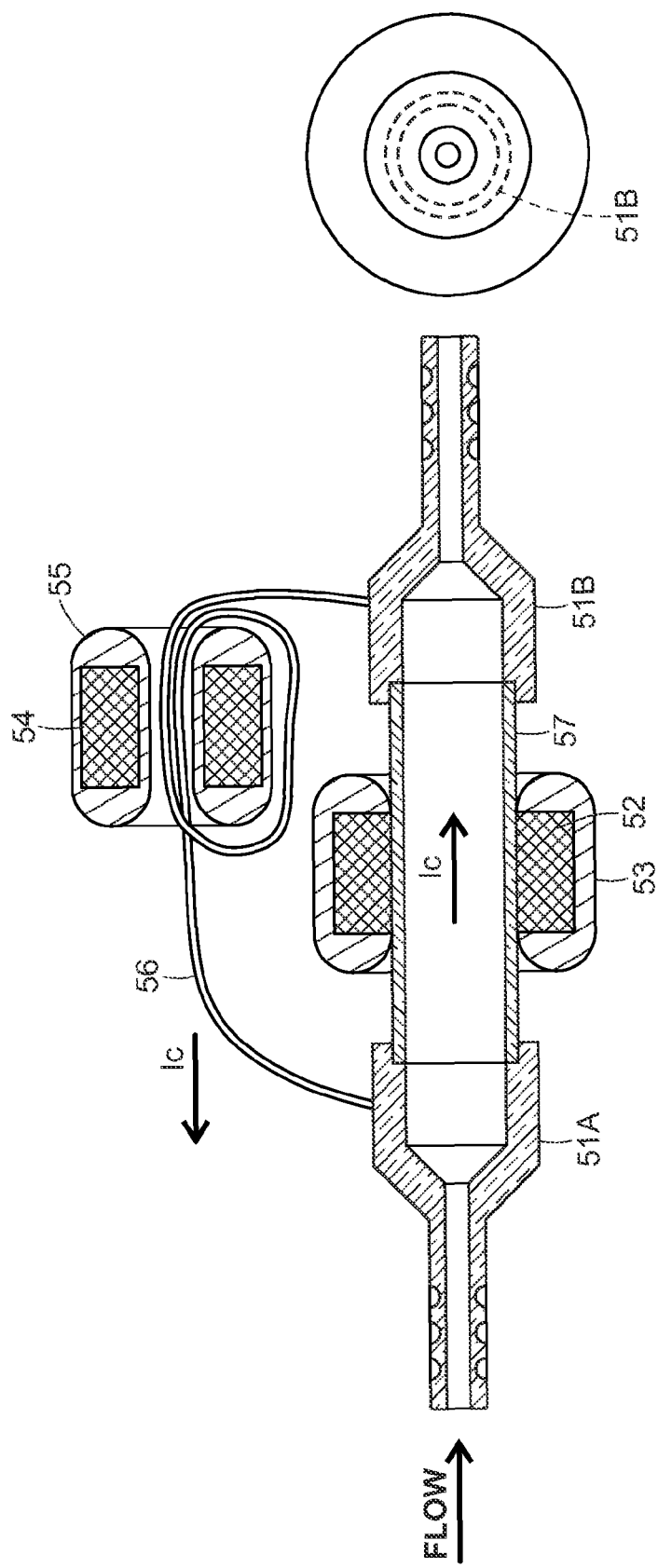
FIG. 10 is a hose-barb implementation of the hybrid electrode and inductive conductivity sensor, in accordance with the present invention.

FIG. 10 illustrates another embodiment of the technology. According to FIG. 10, hose barb tube ends are prepared for the electrodes 51A & 51B (E1 and E2). The hose barb ends 51A & 51B allow the sensor to be "aspirated" by connection of a fluid pump to assist in fluid flow through the sensor, when pumping is needed for biological control. Of course, the outside surfaces of 51A & 51B, in this implementation, must be coated with a dielectric material, to prevent any alternative electrical current return flow path. Toxic collars and pumps have been demonstrated to reduce biological contamination of oceanographic conductivity sensors; the flow pumped is reduced during non-measurement periods, allowing the toxin to leach into and remain in the sensor, thereby minimizing growth of organisms which would tend to foul the tube. The pump evacuates the sensor during measurement periods; this normally used in moored measurement systems, or on "profiling equipment" that drifts in the ocean for periods of time between measurement periods. The HCS sensor, due to its internal field, allows these proven techniques to continue to be used.

Figure 11:
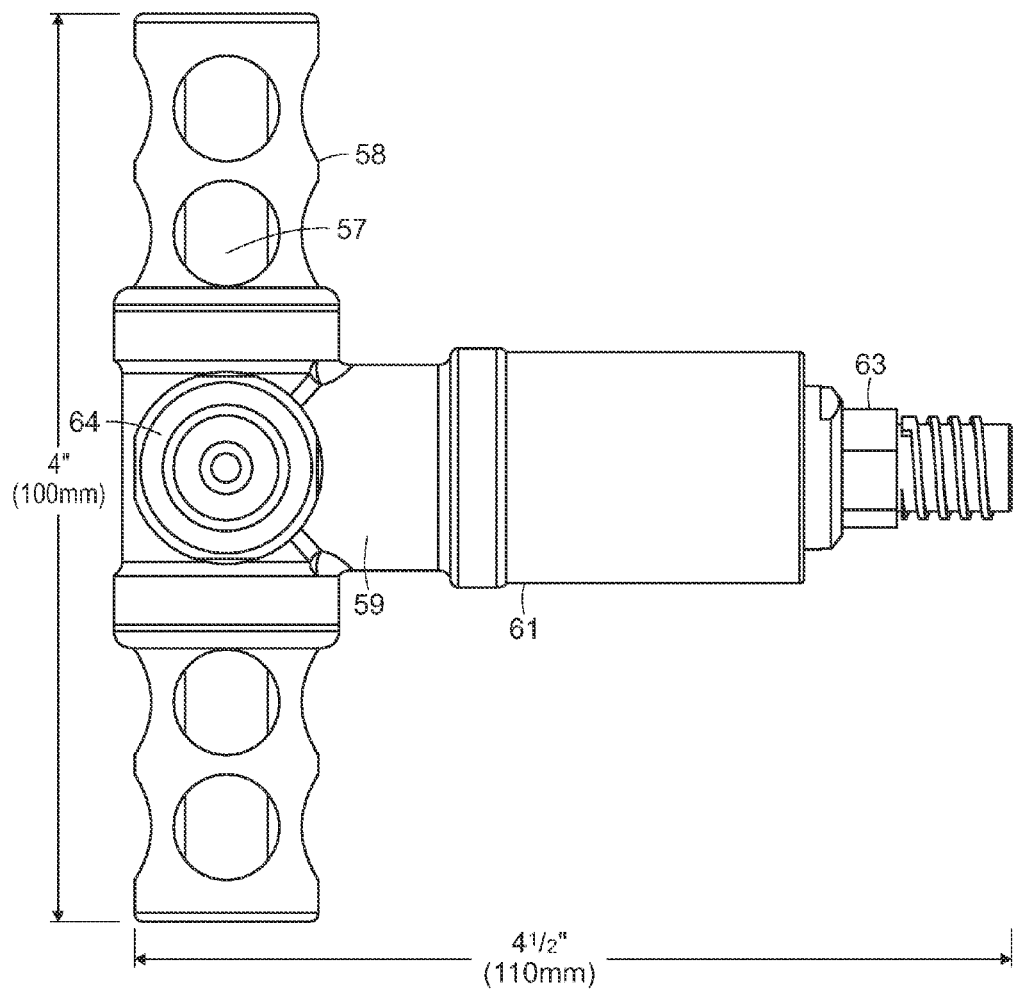
FIG. 11 is an outside view of the hybrid electrode and inductive conductivity sensor, in accordance with the present invention.

The HCS of the present invention has been reduced to a working instrument. Another present implementation of the sensor is illustrated in FIG. 11. The glass tube 57 is protected by end guards 58. The center housing 59 is oil-filled and compensated by diaphragm 64. For example, a suitable oil would be Synthetic Oil #1001A, available from Nye Lubricants of Fairhaven, Mass., USA, and a suitable pressure equalizing diaphragm would be BELLOFRAM CL3-DC-37-H-31, available from Bellofram Corp. of Newell W. Va., USA. The electronics are mounted in pressure-protecting housing 61. User power and data connections are via marine connector 63. The working completed instrument has outside dimensions of 4" (100 mm)×4.5" (112 mm)×2" (50 mm).

External field effects of the sensor, as configured in FIG. 11, have been verified in a mixed salt water bath, by making observations in change of readings due to external physical changes, such as introduction of conducting material, introduction of insulation material, and due to capping one or both ends of the sensor. In this configuration, the HCS sensor reduced external effects to less than +/−0.001 mS/cm. This result is similar to that obtained with the Pederson based Sea Bird Electronics Model SBE-4 internal field sensor in a similar trial, indicating that the HCS sensor current measurement field is essentially fully contained within the internal controlled volume formed by glass tube 57.

Other physical changes, such as variations in sizes, materials, geometry, could also be envisioned by a person having ordinary skill in the oceanographic sensor art; however, it is the combination of technologies that allow accurate open-field measurements of oceanographic seawater electrical conductivity, and thereby enable "equation of state" computations of seawater salinity and density to be made by the HCS.

HCS Electronics

Figure 12:
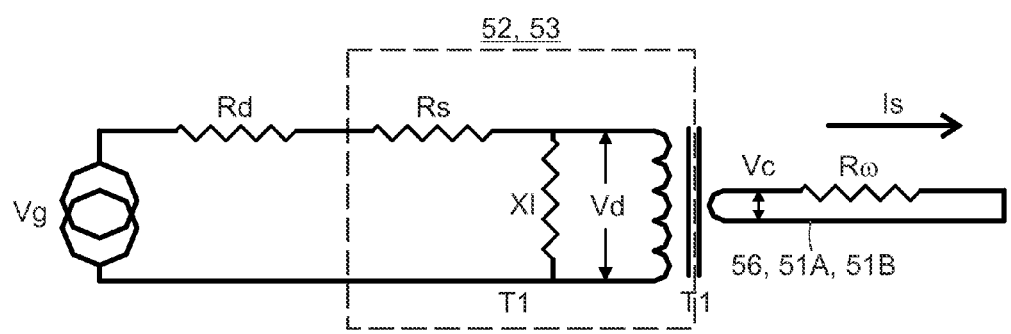
FIG. 12 is an electrical model of the drive core of the hybrid electrode and inductive conductivity sensor, in accordance with the present invention.

The driving-current transformer and its electrical equivalents are shown in FIG. 12. In this figure, the sensor glass tube 57 and the resistance formed by the sea water, the connections to the sea water formed by electrodes 51A & 51B, and the return shorting wire 56 are represented by Rw. The current Is induced in the Rw is in proportion to the magnitude of the drive voltage Vc, as defined by Ohm's law, Is=Vc/Rw. Vc is the result of the single turn formed around the drive core by the enclosed glass tube 57 and Rw as just defined.

In order to make accurate measurements of the electrical current flowing in the sensor, the drive potential Vc, as generated by the transformer T1, must be accurate and stable. The sensor drive potential Vc is directly related to the drive core potential Vd by the fixed winding ratio of the transformer. Hence Vd must be accurate and stable. The electrical potential formed by the drive core is related to the ratios of the complex AC excitation impedance (Xl) of the drive core at the frequency of operation, typically in the audible frequency band (5-15 kiloHertz), where the relationship of electrical conductivity of seawater to salinity is defined, and to the DC winding resistance of the drive winding 53 shown as (Rs), versus, the output impedance of the drive electronic circuit shown as (Rd). If Rd and Rs can be designed such that they are small, compared to Xl, then Vd can be shown to equal Vg, the drive voltage. The drive voltage can be stabilized using traditional voltage references, or by such other means as one having ordinary skill in electronic development would normally employ.

Impedance Rd of the drive circuit can be made very low by the selection of appropriate semiconductor drive elements with very low impedances, such as modern MOSFET (Metal Oxide Semiconductor Field Effect Transistor) switches with ON conductances less than 0.01 ohm (as example MIC-4428, available from MICREL INC. of San Jose, Calif.). The DC winding resistance can be reduced by generally known transformer construction techniques such as the use of Lutz wire, heavy gauge wire, and or multi-conductor wire such that the winding resistance is reduced to a minimum. The AC impedance of the transformer can be increased by the use of compound cores where the aim is simply to increase the amount (cross section) of magnetic materials in the device. The selection of transformer core materials with high initial permeability also serves to increase Xl. Such cores such as those made from SUPERMALLOY (Trademark of Magnetics, Inc. of Pittsburgh Pa.) are generally commercially available. SUPERMALLOY is an alloy composed of nickel (75%), iron (20%), and molybdenum (5%). It is a magnetically soft material. The resistivity of the alloy is 0.6 $\Omega \cdot mm^2/m$ (or $6.0 \times 10^{-7} \Omega \cdot m$). It has an extremely high magnetic permeability (approximately 800000 $N/A^2$) and a low coercivity. SUPERMALLOY is used in manufacturing components for radio engineering, telephony, and telemechanics instruments. Finally, electronic compensation techniques can also be applied to correct for the forward voltage error in the drive transformer.

As shown in FIG. 5, FIG. 6, and FIG. 10, the current sensing core does not need to be mounted near the glass tube. This configuration makes it possible to reduce the size and thermal mass of the resultant sensor, while, at the same time, allowing additional magnetic material to be deployed to reduce errors in the current-sense magnetic circuits; all these modifications are refinements of the invention as described here and, as such, are contained within the scope of the inventive concept, described herein.

Figure 13:
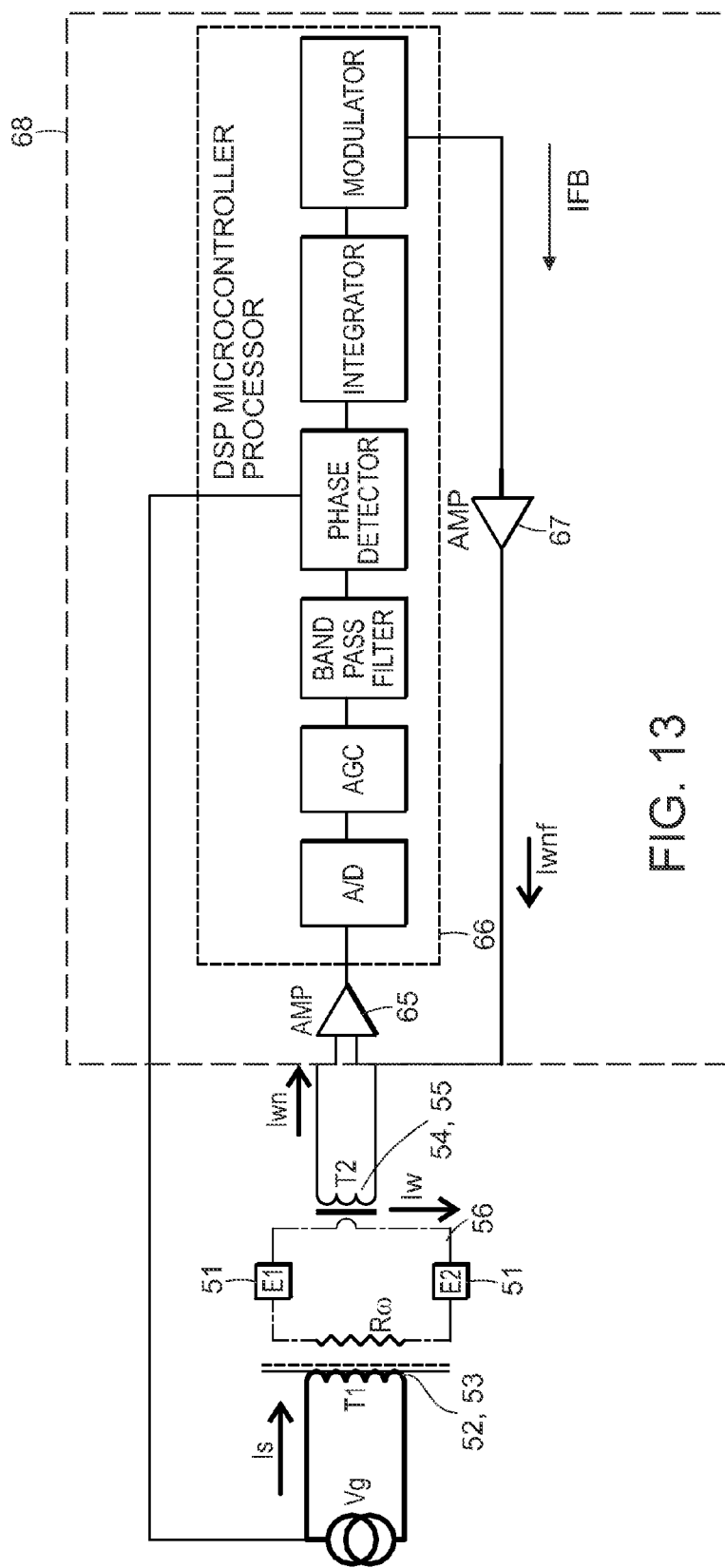
FIG. 13 is an electrical block diagram of the circuitry of the hybrid electrode and inductive conductivity sensor, in accordance with the present invention.

The geometry and performance of the hybrid sensor is further enhanced by a new electronics approach. This approach is named "digital Switching Measurement Technology" or dSMT. A block diagram 68 of the approach is shown in FIG. 13. This is a novel technology that uses AC measurement and feedback techniques. The "d" represents digital. This electronic approach reduces the current measurement errors in the T2 transformer, allowing a minimum of primary turns (56) to be made, further aiding in reducing the total impedance of the shorting function provided by wire (56), and thereby improving the internal field containment of the sensor.

A block diagram of the complete electronics appears in FIG. 13. In essence, the sensor is driven with a traditional AC signal, represented by Vg in the diagram. The driving voltage signal Vg results in a primary AC current Is flowing in T1. This primary current Is results in a secondary winding current Iw, the secondary winding having been formed by the seawater contain in tube 57, and then, as tied together by current collection electrodes 51A & 51B and completing the current path, return wire 56.

Figure 14:
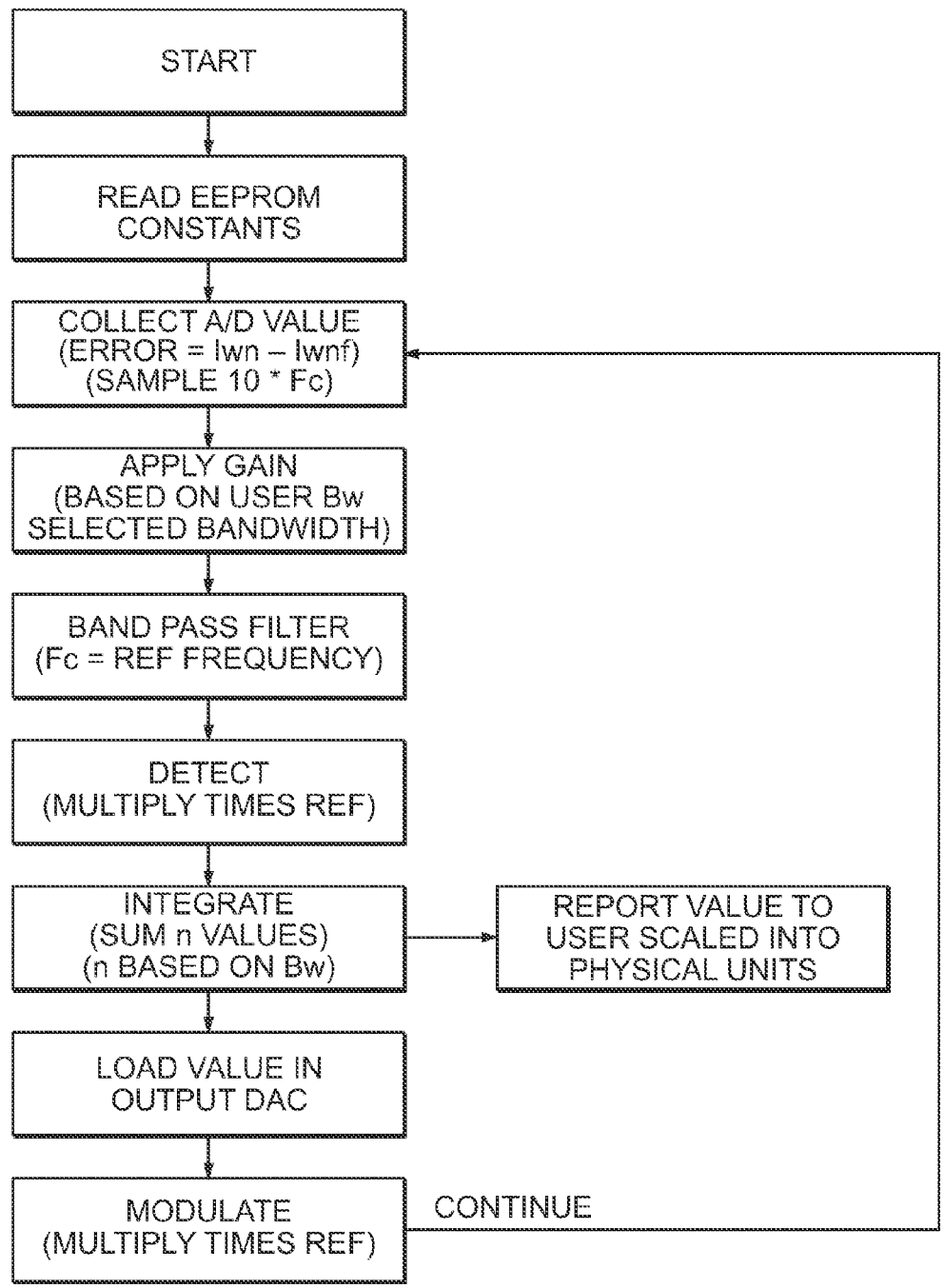
FIG. 14 is a block process control of the steps the hybrid conductivity sensor microcontroller would typically perform in order to process signals.

The magnitude of current Iw, which flows through the sensor, is in inverse proportion to the resistance of the sea water represented by Rw. Shorting wire 56, containing current Iw, is passed around current sensing transformer T2 (with either one or more turns); this winding will be defined as Transformer T2 winding W1. The current Iw flowing in winding W1 induces a current in secondary winding 55 of transformer T2; this current Iwn' which will be in proportion to the current Iw, by a factor corresponding to the turns ratio of the transformer T2. To eliminate current conversion errors in the transformer T2, a current Iwnf equal and opposite to Iwn is electronically fed back into the secondary winding of transformer T2 such that, at balance, the magnetic flux in transformer T2 core 54 is driven to zero. The negative feedback process begins by the amplification of the error signal, the difference between current Iwn less Iwnf, by amplifier 65. The amplified error signal is digitally processed, by the DSP/Microcontroller 66. DSP/Microcontroller 66 starts its process, which is block flow diagramed in FIG. 14, by the analog-to-digital (A/D) conversion of the amplified error signal at the output of amplifier 66. The A/D digitization is performed, at a sampling rate well above the Nyquist frequency called for by the base excitation frequency. The digital representation of the error signal is then digitally automatic gain controlled (AGC), band-pass filtered, gained, phase detected, integrated, and re-modulated to form a negative feedback signal, by the internal DSP 66. The computed output is then used as a negative feedback signal Ifb. The resultant AC signal is amplified by 67, to form a feedback current signal Iwnf, equal and opposite to the current Iwn flowain ing in the secondary W2 winding of transformer T2, which, as demonstrated above, is the result of the current Iw flowing in the Rw seawater in the conductivity sensor. This use of negative feedback results in a feedback current flowing in the winding 55, equal and opposite to the induced current from the current flowing in the sea water; hence, the current-sense core 54 is operated at zero flux, eliminating the possibility of current measurement transfer errors in the sense transformer. This technique eliminates current transformation errors in the current-sense core, due to asymmetry and/or changes to the B-H curve, since the core is operating at average zero flux. The circuit output is then equal to the DC level found at the output of the integrator, as this level is in exact proportion to the Iwnf, hence, in direct relation to Iw, the current flowing in the HCS tube 57. As the value is already a digital value, it needs only to be scaled by constant stored in the DSP/microcontroller 66, and, to be provided to the user in SI units of S/m. Such negative-current feedback systems are well documented and an engineer having ordinary skill in the art of transformer-based current measurement would be able to implement such a circuit. Operating transformer T2 at zero flux eliminates the effect of magnetic changes in the current-sense transformer causing errors in current measurement.

This new electronic approach has several benefits, when applied to the hybrid conductivity sensor of the present invention. Primarily, it allows an interface which is optimized for a four-terminal sensor, which the HCS is. Secondly, the performance is equal to that of traditional AC feedback systems. The size and power of this new technology allow its use from oceanographic delivery platforms such as AUVs and UUVs, profiling floats, and drifters, where size, weight, and, most importantly, minimizing power consumption, are a concern to the researcher or user. As important is that dSMT technology offers very low complexity, digitally configurable resolution, response, and, precision. Each of these can be adjusted by altering constants used in the DSP numerical processor. Additionally, the very low volume allows the electronics to be integrated directly into the sensor, eliminating cables and the problems that occur when sensor and electronics are mounted remotely from each other. This remote mounting can be particularly problematic with reference to the issue of retaining stable physical calibrations.

In the present reduction to practice, the HCS electronic interface is based on a DSP30F microcontroller with built-in DSP, available from the MICROCHIP company of Chandler, Ariz.

To those having ordinary skill in the art of electronic sensor interface development, alternate technologies could also be employed to sense current in the hybrid conductivity sensor; as an example, new innovative Micro-Electrical-Mechanical systems, (MEMs) sensors could replace the current proposed current-sense transformer. As a specific example, a fully developed IC Tunneling Magneto-Resistance (TMR) chip could be used. For example, circuit MMLS43F, available from MultiDimension Technology of Jiangsu Province, PR-China, is suitable.

In this concept, the conductor 56 which ties electrodes 51A & 51B is mounted in a fixed position across the TMR chip, and the current flowing in wire 56 creates an AC magnetic field. This magnetic field is then used as an input to the TMR chip. Magnetoresistance of the magnetic tunnel junction (MTJ), also known as "Tunneling MagnetoResistance" (TMR), is a result of the spin-dependent tunneling effect. The typical structure of an MTJ is two ferromagnetic layers separated by a thin insulating barrier (FM/I/FM). This is sometimes referred to as a "sandwich structure." In sensor applications, one ferromagnetic layer is usually designed such that its magnetization does not move in response to an applied magnetic field. This layer is often called the "pinned" layer. The other ferromagnetic layer is designed such that the magnetization moves easily in response to an applied magnetic field, and this layer is thus often called the "free" layer. Using this basic concept, the relative orientation of the magnetization of the pinned and free layers is representative of the strength and direction of an applied magnetic field. Because the tunneling probability, for electrons to cross the insulating barrier, is dependent on the relative orientation of the free and pinned layer magnetizations, the resistance of an MTJ is indicative of the magnetic field to which the "sandwich" structure has been subjected. In terms of the application of the MTJ, the current flowing in electrode connection wire 56 can be placed in proximity with the MTJ device. The current flowing, as a result of electrical conduction in the sea water, results in Iw flowing in the conductor 56; the current results in a magnetic field which is directly sensed by the MTJ device.

Application of MEM technology to the instrumentation side of the HCS sensor further enhances the technology by attaining reduced size, power and complexity of its implementation.

Various changes, refinements and modifications are possible, within the scope of the inventive concept. Therefore, the invention is not limited to the specific preferred embodiments described above.

What is claimed is:

1. A sensor for measuring electrical conductivity of a fluid containing dissolved ions, comprising
   a generally cylindrical tube (57) of poorly electrically conductive material, having a first, inlet end, an intermediate portion, and a second, outlet end;
   a first toroidal transformer (52) with winding (53) arranged around said tube, near said first end, for applying, during operation, an electromagnetic voltage field to fluid within said tube, to drive a measurement current to flow through fluid in the cylindrical tube (57);
   a first annular electrode (51A), arranged inside said tube, near said first end;
   a second annular electrode (51B), arranged inside said tube, near said second end;
   an electrical conductor (56) interconnecting said first and second electrodes, in order to maintain said electrodes at a common electrical potential with each other, and to provide a lowest-resistance path for the measurement current to flow;
   a second toroidal transformer (54) with winding (55), arranged such that the electrical conductor (56) forms a turn around the second toroidal transformer, to sense a value of current in fluid in said tube (57);
   a source of a time-varying periodic electrical signal, coupled to said first toroidal winding (53); and
   a digital computing device (68), coupled to an output of said second toroidal winding (55), configured to derive, during operation, from an output signal of said second toroidal winding, a current value representing instantaneous electrical conductivity of said fluid within said tube (57).

2. The sensor of claim 1, wherein said time-varying periodic electrical signal is an alternating current (AC) signal.

3. The sensor of claim 1, wherein the digital computing device filters and integrates successively received current values from said second toroidal winding.

4. The sensor of claim 1, wherein said digital computing device (68) comprises
   an analog-to-digital converter;
   a detector configured to detect a phase of said AC signal applied to said drive transformer (52,53); and
   a modulator adapted to generate a feedback current signal, for application to said current sense transformer (54,55), to at least periodically null magnetic flux therein.

5. The sensor of claim 4,
further comprising
   an automatic gain control and a band-pass filter, interposed between said analog-to-digital converter and said phase detector.

6. The sensor of claim 4, further comprising an integrator, interposed between said phase converter and said modulator.

7. The sensor of claim 4, wherein said digital computing device is a digital signal processor (DSP) configured to process conductivity data, temperature data, and pressure data, according to an equation of state algorithm,
   to thereby derive oceanographic salinity and density values.

8. A sensor for measuring electrical conductivity of a fluid containing dissolved ions, comprising
   a generally cylindrical tube (57) of poorly electrically conductive material, having a first, inlet end, an intermediate portion, and a second, outlet end;
   a first toroidal core (52) with winding (53) arranged around said tube, near said first end, for applying, during operation, an electromagnetic field to fluid within said tube, which produces a measurement current flowing in the cylindrical tube (57);
   a first annular electrode (51), arranged inside said tube, near said first end;
   a second annular electrode (51), arranged inside said tube, near said second end;
   an electrical conductor (56) interconnecting said first and second electrodes, in order to maintain said electrodes at a common electrical potential with each other, and, to provide the lowest resistance path for the measurement current to flow;
   a second toroidal core (54) with winding (55), arranged such that the electrical conductor (56) forms a turn around the second toroidal core;
   a source of a time-varying periodic electrical signal, coupled to said first toroidal winding (53);
   a pressure-protective housing (61) mechanically connected to said tube (57), said housing (61) surrounding a digital computing device (68), coupled to an output of said second toroidal winding (55), configured to derive, during operation, from an output signal of said second toroidal winding (55), a current value representing instantaneous electrical conductivity of said fluid within said tube.

9. The sensor of claim 8, wherein said pressure-protecting housing (59, 61) is mechanically coupled to an intermediate portion of said tube (57) and extends laterally therefrom.

10. The sensor of claim 8, further comprising
   a generally cylindrical first end guard concentrically surrounding said inlet end of said tube;
   a generally cylindrical second end guard concentrically surrounding said outlet end of said tube; and
   an oil-filled central housing (59) interposed between said tube (57) and said pressure-protecting housing (61) surrounding said digital computing device.

* * * * *